United States Patent [19]

Schulte-Elte

[11] 4,280,934

[45] Jul. 28, 1981

[54] CYCLOPENTANE DERIVATIVES USEFUL AS PERFUMING AGENTS

[75] Inventor: Karl-Heinrich Schulte-Elte, Onex, Switzerland

[73] Assignee: Firmenich SA, Geneva, Switzerland

[21] Appl. No.: 104,404

[22] Filed: Feb. 17, 1979

Related U.S. Application Data

[63] Continuation of Ser. No. 808,688, Jun. 21, 1977, abandoned.

[30] Foreign Application Priority Data

Jun. 30, 1976 [CH] Switzerland ........................ 8343/76

[51] Int. Cl.[3] ........................ A61K 7/46

[52] U.S. Cl. ........................ 252/522 R; 560/122

[58] Field of Search ........................ 252/522 R

[56] References Cited

U.S. PATENT DOCUMENTS 1,965,792 7/1934 Chaux ........................ 560/118

OTHER PUBLICATIONS

Linstead et al., J. Chem. Soc., 610-614, 1934.

Kou et al., J. Chem. Soc., 2461-2463, 1932.

Cristol et al., J. Org. Chem., 27, p. 293, 1962.

*Primary Examiner*—John F. Niebling

*Attorney, Agent, or Firm*—Pennie & Edmonds

[57] ABSTRACT

Cyclopentane derivatives useful as odor-modifying ingredients for manufacturing perfumes and perfumed products and perfume compositions containing same.

7 Claims, No Drawings

CYCLOPENTANE DERIVATIVES USEFUL AS PERFUMING AGENTS

This is a continuation of application Ser. No. 808,688 filed June 21, 1977, now abandoned.

SUMMARY OF THE INVENTION

The invention relates to a method for improving, enhancing or modifying the odoriferous properties of perfumes or perfumed products which comprises adding thereto an effective amount of at least one compound having the formula

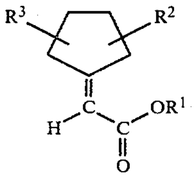

(I)

wherein symbol $R^1$ represents a linear, branched, saturated or unsaturated hydrocarbon radical containing 1 to 6 carbon atoms and wherein each of symbols $R^2$ and $R^3$, the same or different, represents a hydrogen atom or a lower alkyl radical.

In the generic formula given hereinabove, symbol $R^1$ represents an alkyl radical such as for example a methyl, an ethyl, a propyl, an isopropyl, a butyl, a sec-butyl, a ter-butyl, a pentyl, a sec-pentyl, an isopentyl, a hexyl, an isohexyl, a vinyl or an allyl radical.

Symbol $R^1$ preferentially represents a lower linear hydrocarbon radical, more preferentially a methyl radical.

The invention further relates to a perfume base, a perfume composition or a perfumed article containing as an odoriferous active ingredient at least one compound having formula (I) as set forth hereinabove in combination with a support, a perfume coingredient, a diluent or an excipient.

The invention relates moreover to certain new cyclopentane derivatives of formula (I).

BACKGROUND OF THE INVENTION

Among the alicyclic compounds of formula (I), there are a few of prior known structure. These are namely, methyl-, ethyl- and t-butyl cyclopentylidene acetate [$R^2=R^3=H$; $R^1$=methyl, ethyl and t-butyl, respectively, in formula (I)], which compounds have been described in J.Chem.Soc., 1934, 610; idem 1932, 2461 and J.Org.Chem., 27,293(1962), respectively. It has to be noted however that the cited literature does not mention nor suggest any possible utility of the given compounds as perfuming ingredients. Hitherto, their olfactive properties have not been recognized and consequently no attention has been devoted by the man in the art to their utilization.

PREFERRED EMBODIMENTS OF THE INVENTION

We have now discovered that the cyclopentane derivatives of formula (I) possess valuable odoriferous properties and could be advantageously utilized in the perfume industry. They are characterized by a fruity and flowery fragrance partially reminiscent of the odour of benzoic or salicyclic acid ester derivatives. Among the compounds of formula (I), methyl cyclopentylidene acetate presents particularly advantageous odour characters of remarkable strength and "lift", reminiscent of the odour of ylang-ylang oil. Methyl cyclopentylidene acetate is a compound of great olfactive and chemical stability in most of the media commonly encountered not only in fine perfumery but also in technical articles such as soaps, shampoos, bleaching powders, detergents, dish washing powders and household materials in general. This is certainly of great advantage in all those cases where, due to its instability, ylang-ylang cannot be conveniently used; thus, methyl cyclopentylidene acetate and the other compounds of formula (I) can find a much broader range of use than the said natural oil.

When compounds (I) are used in accordance with the present invention, for example as ingredients for the manufacture of perfume compositions, interesting olfactive effects can be achieved by the use of proportions comprised between about 0.05 and 5% by weight of the total weight of the said composition. Of course, these proportions can be higher than the above indicated values whenever compounds (I) enter in a perfume base or when special odoriferous effects are derived.

As indicated above, some of the compounds designated by formula (I) are new; these namely include the following of particular interest:

n-propyl cyclopentylidene acetate,
isopropyl cyclopentylidene acetate,
n-butyl cyclopentylidene acetate,
iso-butyl cyclopentylidene acetate, n-pentyl cyclopentylidene acetate,
n-hexyl cyclopentylidene acetate,
allyl cyclopentylidene acetate and
methyl 3,4-dimethyl-cyclopentylidene acetate.

The compounds of formula (I) can be readily prepared according to current techniques, for instance following the synthetic procedure described in the above state of the art. Typically, compounds (I) can be prepared by reacting a cyclopentanone derivative of formula

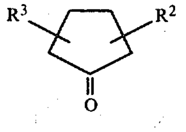

(II)

wherein $R^2$ and $R^3$ have the meaning defined for formula (I), with a halo-ester of formula $$Hal{-}CH_2{-}COOR^1 \qquad (III)$$

wherein Hal designates a halogen atom, such as chlorine or bromine, and $R^1$ represents a hydrocarbon radical as indicated above.

The said reaction is effected according to the so-called Horner-Wittig procedure as described for instance by H. O. House, Modern Synthetic Reactions, W. A. Benjamin Inc., 1972, p. 690. The first step of the above said process consists in reacting compounds (III) with a trialkyl phosphite, e.g. trimethyl or triethyl phosphite, typically by warming them up, optionally in the presence of an inert solvent to yield the corresponding dialkylphosphono-acetate. This latter compound, usually isolated from the reaction mixture, is then condensed with cyclopentanone (II) in the presence of a strong base and in an organic solvent medium. Suitable strong bases include aryl- or alkyl-lithium, e.g. butyllithium, an alkali metal alkoxide, such as sodium methoxide, or an alkali metal hydride or amide, such as sodium or potassium hydride or amide. The condensation with cyclopentanone (II) is carried out in an inert organic solvent such as an aliphatic or aromatic hydrocarbon or an ether, e.g. diethylether, diisopropylether or tetrahydrofuranne. It is also possible to operate in the presence of an additional solvent, dimethylsulfoxide, dimethylformamide or phosporic acid tri-N,N-dimethylamide (HMPT). In such a way starting from cyclopentanone and methyl chloroacetate, it is possible to synthetize methyl cyclopentylidene acetate. Compounds (I) wherein symbol $R^1$ represents a methyl radical constitute useful starting material for the preparation of the corresponding higher homologues via a transesterification reaction. Thus, starting from methyl cyclopentylidene acetate it was possible to obtain with good yields, e.g. ethyl and propyl cyclopentylidene acetate.

The invention is better illustrated by but not limited to the following examples wherein the temperatures are indicated in degrees centigrade and the abbreviations have the meaning common in the art.

EXAMPLE 1

Methyl cyclopentylidene acetate (a) 682 g (5.5 M) of trimethylphosphite have been slowly added (2½h) to 272 g (2.5 M) of methyl chloroacetate preliminarly heated to 118°. The temperature of the reaction mixture raised at the end of the addition to 125° and was kept at this value for 2 h, whereupon 962 g of raw material was isolated on distillation. A further distillation has enabled to obtain 344 g (yield 75%) of methyl-dimethylphosphonacetate having b.p. 125°/8 Torr.

(b) 137 g of the thus obtained phosphonoacetate were slowly added to a mixture of 750 ml of anhydrous diisopropyl-ether, 75 g of HMPT and 18.5 g of sodium hydride. The addition was effected under nitrogen and at a temperature of 20°-25°, then 63 g of cyclopentanone dissolved in 125 ml of diisopropylether were added to the obtained mixture. The whole was heated at 70°-72° during 3 h, whereupon, after cooking, the excess of sodium hydride was decomposed by methanol. Ether extraction, washing, drying and evaporation of the volatile compounds enabled to obtain 103 g of raw methyl cyclopentylidene acetate.

Fractional distillation of this material gave 96 g (yield 92%) of the derived product having b.p. 57-9°/8 Torr.

$n_D^{20}=1.4752$; $d_4^{20}=1.005$.

IR=1720, 1650 $cm^{-1}$.

NMR 1.57-1.84(4H,m); 2.30-2.91(4H,m); 3.60 (3H,s); 5.76(1H,m) δ ppm.

MS: M+=140(100); m/e: 125(12), 109(85), 97(8), 79(85), 67(48), 53(52), 41(56).

EXAMPLE 2

Ethyl cyclopentylidene acetate

A mixture of 20 g of methyl cyclopentylidene acetate, 100 g of ethyl acetate and 2 g of aluminium isopropylate was heated at reflux in a reaction vessel equipped with a distillation column. The methyl acetate which builts up during the reaction is taken off as soon as formed by distillation. Heating was interrupted once the distillation came to an end and the desired ester was collected by fractional distillation. It was thus possible to obtain ethyl cyclopentylidene acetate at b.p. 63°-40°/8 Torr with an yield of 90%.

IR: 1712, 1655 and 855 $cm^{-1}$.

NMR: 1.21(3H,t,J=6 cps); 4.08(2H,9,J=6 cps); 5.70(1H,m) δppm.

MS: M+=154(78); m/e: 140(3), 126(78), 109(100), 97(30), 81(75), 67(80), 41(45).

EXAMPLE 3 n-Propyl cyclopentylidene acetate

By substituting n-propyl acetate for ethyl acetate and operating in the same reaction conditions as indicated in Example 2 above, it was possible to obtain the title compound with an analogous yield. The n-propyl ester had b.p. 67°-8°/8 Torr.

IR: 1710, 1650, 855 $cm^{-1}$.

NMR: 0.98(3H,t,J=6 cps); 3.99(2H,t,J=6 cps); 5.72(1H,m) δ ppm.

MS: M+=168(20); m/e: 150(1), 126(100), 109(80), 81(45), 67(50), 41(50).

EXAMPLE 4

Allyl cyclopentylidene acetate (a) A mixture of 217 g of methyl chloroacetate, 145 g of allyl alcohol and 10 g of benzenesulphonic acid was heated to 100°-130° and subjected at first to distillation at atmospheric pressure, followed by a distillation under vacuum (13 Torr). It was thus possible to collect 196 g of allyl chloroacetate having b.p. 51°-53°/13 Torr.

(b) 191 g of trimethylphosphite were added dropwise under stirring to 188 g of allyl chloroacetate (2½ h) preliminarly heated to 118°. The reaction mixture was kept at this temperature for 4h, whereupon it was subjected to a distillation to give 205 g of allyl dimethylphosphono-acetate, b.p. 118°/0.1 Torr.

(c) 100 g of the obtained phosphono-acetate were treated with an equivalent amount of cyclopentanone as described in Example 1, Section b. The desired allyl cyclopentylidene acetate was thus obtained in a 63% yield. B.p. 74°/7.5 Torr.

IR: 3070, 1710, 1650, 900 and 910 $cm^{-1}$.

NMR: 1.50-1.76(6H); 4.48-4.63(2H,2s); 5.07-6.31 (4H,m) δ ppm.

MS: M+=166(11); m/e: 151(1), 137(13), 125(66), 109(100), 93(9), 79(72), 67(16), 53(30), 41(79), 27(27).

EXAMPLE 5

Methyl 3,4-dimethyl-cyclopentylidene acetate

By proceeding as indicated in Example 4 and replacing cyclopentanone by 3,4-dimethyl-cyclopentanone, the title compound was obtained with a yield of 89%. The obtained compound consisted of a 1:1 mixture of isomers A and B whose analytical characters were as follows:

isomer A

IR: 1710 and 1640 $cm^{-1}$.

NMR: 0.87-1.08(6H); 4.60(3H,s); 5.67(1H,m) δ ppm.

MS: M+=168(25); m/e: 153(100), 137(16), 121(33), 93(34), 79(13), 67(16), 53(12), 41(26), 27(15).

isomer B

IR: 1710 and 1640 $cm^{-1}$.

NMR: 0.80-0.98(6H,2d); 3.56(3H,s); 5.57-5.76(1H,m) δ ppm.

MS: M+=168(26); m/e: 153(100), 137(17), 121(34), 112(7), 97(36), 79(14), 67(17), 53(13), 41(28), 27(15).

EXAMPLE 6

A base perfume composition of "flowery" type is obtained by mixing together the following ingredients (parts by weight):

| | |
|---|---|
| Synthetic jasmin | 200 |
| Phenylethanol | 150 |
| Rosewoodoil of Brazil | 100 |
| t-Butylcyclohexyl acetate | 80 |
| Trimethyl-cyclododecatriene epoxide | 60 |
| 2,5,9-Trimethyl-4,9-dien-1-al 10%* | 40 |
| Citronellol | 40 |
| 4-Isopropyl-cyclohexylmethanol(1) | 40 |
| Iralia ®, (Firmenich SA) | 40 |
| 1-(3,3-Dimethyl-cyclohex-6-en-1-yl)-pent-4-en-1-one 1%* | 30 |
| 2,4-Dimethyl-cyclohex-3-ene-carbaldehyde 10%* | 30 |
| 1,1-Dimethyl-4-acetyl-6-t-butylindane | 20 |
| Lavandin oil | 20 |
| cis-Jasmone 10%* | 20 |
| Isocamphyl-cyclohexanol | 10 |
| Methyl dihydrojasmonate | 10 |
| 2-Methyl-3-(5-isopropenyl-2-methyl-cyclopent-1-en-1-yl)-propyl acetate(2) | 10 |
| Total | 900 |

*in diethyl phthalate
(1)Firmenich SA, see UK Pat. No. 1,416,658
(2)Firmenich SA, see Swiss Pat. No. 566,113.

By adding to 90 g of the above given perfume base, 15 g of methyl cyclopentylidene acetate at 10% in diethyl phthalate, there was obtained a novel composition which possessed, when compared with the base composition, an original top note and a fresher and more lifting character reminiscent of the odour developed by the oil of ylang-ylang. By replacing in the above example, methyl cyclopentylidene acetate by ethyl or n-propyl cyclopentylidene acetate, analogous effects were observed.

EXAMPLE 7-12

Methyl cyclopentylidene acetate was used to perfume standard articles in the concentration given below. The stability and the colour of the perfumed articles is indicated in the following table:

| Ex. | Article | Concentration by weight | Temperature [°C.] | Performance stab./colour |
|---|---|---|---|---|
| 7 | Eau-de-Cologne | 5% in ethanol | 22 (3 months)<br>40 (1 month) | S/N*<br>S/N |
| 8 | Soap | 1% | 22 (3 months)<br>40 (1 month) | S/N<br>S/N |
| 9 | Non-fatty cream | 0.4% | 22 (3 months) | S/N |
| 10 | Talc powder | 1% | 22 (3 months) | S/N |
| 11 | Anti-perspirant aerosol | 1.2% | 22 (3 months) | S/N |
| 12 | Shampoo | 0.5% | 22 (3 months)<br>40 (1 month) | S/N<br>S/N |

*S = stable
N = normal

The perfume ingredient proved also stable to prolonged UV irradiation.

What I claim is:

1. The method for improving or enhancing the odoriferous properties of perfumes or perfumed products which consists essentially of adding thereto an effective amount of at least one substantially pure compound characterized by fruity or flowery fragrance and having the formula

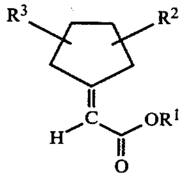

(I)

wherein the symbol $R^1$ represents a linear, branched, saturated or unsaturated hydrocarbon radical containing 1 to 6 carbon atoms and wherein each of the symbols $R^2$ and $R^3$ are the same or different and represents a hydrogen atom or a lower alkyl radical.

2. The method according to claim 1 wherein $R^1$ represents a lower linear hydrocarbon radical.

3. The method according to claim 2 wherein $R^1$ is methyl.

4. A perfume base, a perfume composition or a perfumed article which consists essentially of having added thereto as an odoriferously active ingredient at least one substantially pure compound having the formula (I) as set forth in claim 1, in combination with a support, a perfume coingredient, a diluent or an excipient.

5. A perfume base, a perfume composition for a perfumed article according to claim 4, wherein the compound of formula (I) is added at a concentration of between about 0.05 and 5% by weight based on the total weight of the perfumed material.

6. A perfume base, a perfume composition of a perfumed article according to claim 4 wherein $R^1$ represents a lower linear hydrocarbon radical.

7. A perfume base, a perfume composition or a perfumed article according to claim 6 wherein $R^1$ is methyl.

* * * * *